US012082974B2

(12) United States Patent
Chamberlain et al.

(10) Patent No.: US 12,082,974 B2
(45) Date of Patent: Sep. 10, 2024

(54) ULTRASOUND SCANNER THAT SUPPORTS HANDSET WIRELESS NETWORK CONNECTIVITY

(71) Applicants: FUJIFILM SONOSITE, INC., Bothell, WA (US); FUJIFILM CORPORATION, Tokyo (JP)

(72) Inventors: Craig Chamberlain, Seattle, WA (US); Christopher Howard, Seattle, WA (US); Harald Fiedler, Mukilteo, WA (US); Derek Jensen, Mountlake Terrace, WA (US); Katsuya Yamamoto, Kanagawa (JP); Hiroshi Murakami, Kanagawa (JP); David Hoglund, Harleysville, PA (US)

(73) Assignees: FUJIFILM SONOSITE, INC., Bothell, WA (US); FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 17/830,066

(22) Filed: Jun. 1, 2022

(65) Prior Publication Data
US 2023/0389895 A1 Dec. 7, 2023

(51) Int. Cl.
A61B 8/00 (2006.01)
(52) U.S. Cl.
CPC .......... A61B 8/4472 (2013.01); A61B 8/4254 (2013.01); A61B 8/461 (2013.01); A61B 8/467 (2013.01); A61B 8/565 (2013.01)
(58) Field of Classification Search
CPC ..... A61B 8/4472; A61B 8/4254; A61B 8/461; A61B 8/467; A61B 8/565
See application file for complete search history.

(56) References Cited

U.S. PATENT DOCUMENTS 11,627,939 B2 * 4/2023 Park ..................... H02J 7/0045
600/459
2013/0158397 A1 * 6/2013 K ............................ G16Z 99/00
600/437

(Continued)

FOREIGN PATENT DOCUMENTS

CN 114145770 A 3/2022
KR 1020160066393 A 6/2016

OTHER PUBLICATIONS

PCT International Search Report and Written Opinion for PCT/US2023/015528, mailed Jul. 6, 2023, 10 pages.

Primary Examiner — Alexei Bykhovski
(74) Attorney, Agent, or Firm — Womble Bond Dickinson (US) LLP

(57) ABSTRACT

Systems and methods to provide an ultrasound scanner that supports handset wireless network connectivity are described. An ultrasound scanner includes a transducer system that generates, as part of an ultrasound examination, ultrasound data based on reflections of ultrasound signals transmitted by the transducer system. The ultrasound scanner includes a first transceiver that communicates, over a first communication link, the ultrasound data to a display device that displays an ultrasound image based on the ultrasound data. The ultrasound scanner includes one or more additional transceivers that communicate, over a one or more additional communication links and simultaneously with the first transceiver communicating the ultrasound data over the first communication link, the ultrasound data through an access point of a care facility administering the ultrasound examination.

20 Claims, 6 Drawing Sheets

(56) References Cited

U.S. PATENT DOCUMENTS

| | | | |
|---|---|---|---|
| 2015/0313578 A1* | 11/2015 | Yu | A61B 8/4254 |
| | | | 600/459 |
| 2016/0174937 A1 | 6/2016 | Bakshi et al. | |
| 2016/0278739 A1 | 9/2016 | Pelissier et al. | |
| 2018/0249986 A1* | 9/2018 | Lee | A61B 8/145 |
| 2019/0313999 A1* | 10/2019 | Kim | A61B 8/488 |
| 2019/0365356 A1* | 12/2019 | Kurita | G16H 40/67 |
| 2020/0085408 A1* | 3/2020 | Lemaitre | A61B 8/54 |
| 2020/0281565 A1* | 9/2020 | Yee | A61B 8/465 |
| 2021/0196243 A1* | 7/2021 | Osumi | A61B 8/5207 |
| 2021/0259664 A1* | 8/2021 | Hare | A61B 8/463 |
| 2021/0312652 A1* | 10/2021 | Padwal | A61B 8/4461 |
| 2022/0008141 A1* | 1/2022 | Chopra | A61B 6/461 |
| 2022/0062661 A1* | 3/2022 | Tyler | A61B 5/369 |
| 2022/0133281 A1 | 5/2022 | Hattori et al. | |
| 2022/0175340 A1* | 6/2022 | Xu | A61B 8/4444 |
| 2023/0263502 A1* | 8/2023 | Tirumalai | A61B 8/54 |
| | | | 600/437 |

\* cited by examiner

ULTRASOUND SCANNER THAT SUPPORTS HANDSET WIRELESS NETWORK CONNECTIVITY

Embodiments disclosed herein relate to ultrasound systems. More specifically, embodiments disclosed herein relate to an ultrasound scanner that supports handset wireless network connectivity.

BACKGROUND

Medical devices increasingly maintain persistently wired and/or wireless connections to hospital networks to support the seamless transfer of health information from the device into other applications, such as a patient's electronic health record. This connection increasingly supports the communication of device performance data and remote device management by the hospital IT team and/or device manufacturer enabling preventative maintenance, cyber security updates, etc.

In conventional wireless ultrasound systems, in order to assess a patient, a user needs to turn on the scanner and disconnect the handset or ultrasound device from the hospital WLAN to make a wireless connection on the handset or ultrasound device available to the scanner. The user would then connect the handset or ultrasound device to the scanner. Once the wireless connection between the scanner and the handset or ultrasound device is established, the user can assess the patient.

Once the assessment is complete, to upload any acquired data from the assessment to the patient's medical records, the connection process needs to be reversed. That is, the user needs to disconnect the handset or ultrasound device from the scanner and reconnect the handset or ultrasound device to the hospital WLAN. These disconnection and connection cycles are time consuming, energy inefficient, and result in sub-optimal patient care.

SUMMARY

Systems and methods to provide an ultrasound scanner that supports handset wireless network connectivity are described. In some embodiments, an ultrasound scanner includes a transducer system configured to generate, as part of an ultrasound examination, ultrasound data based on reflections of ultrasound signals transmitted by the transducer system. The ultrasound scanner includes a first transceiver that is implemented at least partially in hardware and that communicates, over a first communication link, the ultrasound data to a display device that displays an ultrasound image based on the ultrasound data. The ultrasound scanner includes one or more additional transceivers that are implemented at least partially in the hardware that communicates, over one or more additional communication links, the ultrasound data through an access point of a care facility administering the ultrasound examination. The one or more additional transceivers communicates the ultrasound data over the one or more additional communication links simultaneously with the first transceiver communicating the ultrasound data over the first communication link.

In some embodiments, an ultrasound system includes at least one display device that is configured to display an ultrasound image based on ultrasound data. An ultrasound scanner is coupled to at least one display device. The ultrasound scanner is configured to, as part of an ultrasound examination, generate the ultrasound data based on reflections of ultrasound signals transmitted by the ultrasound scanner. The ultrasound scanner is configured to communicate, over a first communication link, the ultrasound data to at least one display device. The ultrasound scanner is also configured to communicate, over one or more additional communication links, the ultrasound data through an access point of a care facility administering the ultrasound examination. The ultrasound scanner is configured to communicate the ultrasound data over the one or more additional communication links simultaneously with communicating the ultrasound data over the first communication link.

In some embodiments, a method is implemented by an ultrasound system to perform an ultrasound examination. The method includes generating ultrasound data based on reflections of ultrasound signals transmitted by the ultrasound scanner and communicating, over a first communication link, the ultrasound data to at least one display device configured to display an ultrasound image based on the ultrasound data. The method also includes communicating, over one or more additional communication links and simultaneously with communicating over the first communication link, the ultrasound data through an access point of a care facility administering the ultrasound examination.

Other systems, machines, and methods for handset wireless network connectivity are also described.

BRIEF DESCRIPTION OF THE DRAWINGS

The appended drawings illustrate examples and are, therefore, exemplary embodiments and not considered to be limiting in scope.

DETAILED DESCRIPTION

Figure 1:
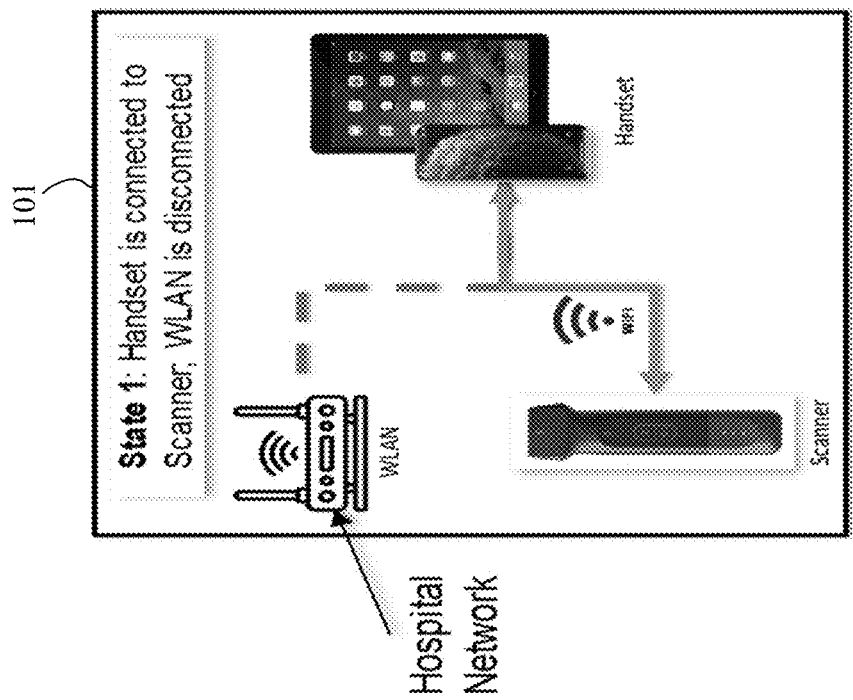
FIG. 1 is a view illustrating connectivity states for a conventional ultrasound system that includes a handset and an ultrasound probe.

Systems and methods to provide an ultrasound scanner that supports handset wireless network connectivity are described. In some embodiments, an ultrasound scanner includes a transducer system configured to generate, as part of an ultrasound examination, ultrasound data based on reflections of ultrasound signals transmitted by the transducer system. A first transceiver is implemented at least partially in hardware of the ultrasound scanner and configured to communicate, over a first communication link, the ultrasound data to a display device that is configured to display an ultrasound image based on the ultrasound data. A second transceiver is implemented at least partially in the hardware of the ultrasound scanner and configured to communicate, over a second communication link, the ultrasound data through an access point of a care facility administering the ultrasound examination. The second transceiver communicates the ultrasound data over the second communication link simultaneously with the first transceiver communicating the ultrasound data over the first communication link.

Embodiments described herein are directed to ultrasound systems that include a scanner that bridges a WLAN connection to an ultrasound device and/or a handset (e.g., a display device) and operates as a hub for accessing to a hospital network while scanning a patient. Such embodiments enable access to the hospital network while scanning the patient, real-time upload of scan data directly into hospital picture archiving systems, real-time use of tele-scanning/telemedicine, real-time use of video and voice over IP (VOIP) services to support translation/communication with the patient, real-time communication between the scanner and remote monitoring and management services, real-time access to cloud-based educational content, and real-time use of cloud-based artificial intelligence (AI) and other cloud-based services.

Reference in the specification to "one embodiment" or "an embodiment" means that a particular feature, structure, or characteristic described in conjunction with the embodiment can be included in at least one embodiment. The appearances of the phrases "in one embodiment" or "in an embodiment" in various places in the specification do not necessarily all refer to the same embodiment. The processes depicted in the figures that follow are performed by processing logic that comprises hardware (e.g., circuitry, dedicated logic, etc.), software, or a combination of both. Although the processes are described below in terms of some sequential operations, it should be appreciated that some of the operations described may be performed in a different order. Moreover, some operations may be performed in parallel rather than sequentially.

In the specification, the term "and/or" describes three relationships between objects that may exist. For example, A and/or B may represent the following cases: only A exists, both A and B exist, and only B exist, where A and B may be singular or plural.

As set forth above, conventional ultrasound systems suffer from a connectivity constraint issue that arises while trying to maintain simultaneous data connections among a wireless ultrasound transducer apparatus (scanner), a wireless compute and visualization system, such as smartphone or tablet (handset), and a wireless local area network (WLAN). This connectivity issue is applicable to any medical device seeking to support simultaneous data acquisition, wireless transfer of data for processing on a handset, and connection to a WLAN. Typically, common consumer handsets, for example, iPhones, limit Wi-Fi connectivity to a single 3rd party wireless connection (e.g., scanner or WLAN).

FIG. 1 is a view 100 illustrating connectivity states for a conventional ultrasound system that includes a handset (e.g., a smart phone, tablet) and an ultrasound scanner (e.g., an ultrasound probe). As shown in insert 101 of FIG. 1, in connectivity state 1, the handset is wirelessly connected to the scanner and is disconnected from a wireless local area network (WLAN) (e.g., a WLAN network within a hospital facility or another setting where ultrasound use is supporting healthcare activities). The wireless connection to the scanner prevents the handset from connecting to the WLAN and performing all functionality that requires persistent connection to the WLAN. This inability to persistently connect to the WLAN means the following device use cases are inhibited or completely prevented until a WLAN connection can be reestablished: the real-time, direct upload of scan data into hospital picture archiving systems; the use of tele-scanning/telemedicine while actively scanning the patient; the use of video and voice over internet protocols (VOIP) services to support translation/communication with the patient while scanning the patient; and real-time communication between the scanner and remote monitoring and management services, real-time access to cloud-based educational content, and real-time use of cloud-based artificial intelligence (AI) and other cloud-based services.

As shown in insert 102 of FIG. 1, in connectivity state 2, the handset is connected to the WLAN and is disconnected from the scanner. The wireless connection to the WLAN prevents the handset from connecting to the scanner and assessing a patient. This inability to connect to the scanner means the following device use cases are inhibited or completely prevented: the real-time, direct upload of scan data into hospital picture archiving systems; the use of tele-scanning/telemedicine while actively scanning the patient; the use of video and VOIP services to support translation/communication with the patient while scanning the patient; and real-time communication between the scanner and remote monitoring and management services. As shown in inserts 101 and 102, the scanner is configured as an end node. The connectivity constraint also applies when trying to connect a scanner to other devices with one connection Wi-Fi, such as current generation compact ultrasound machines (devices).

Figure 2:
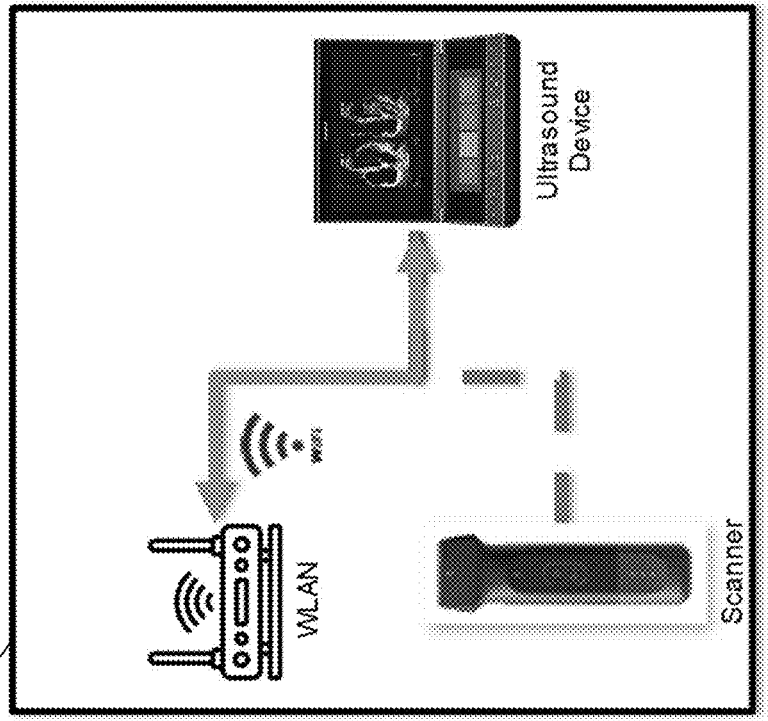
FIG. 2 is a view illustrating connectivity states for another conventional ultrasound system that includes an ultrasound device and a scanner.
Figure 2:
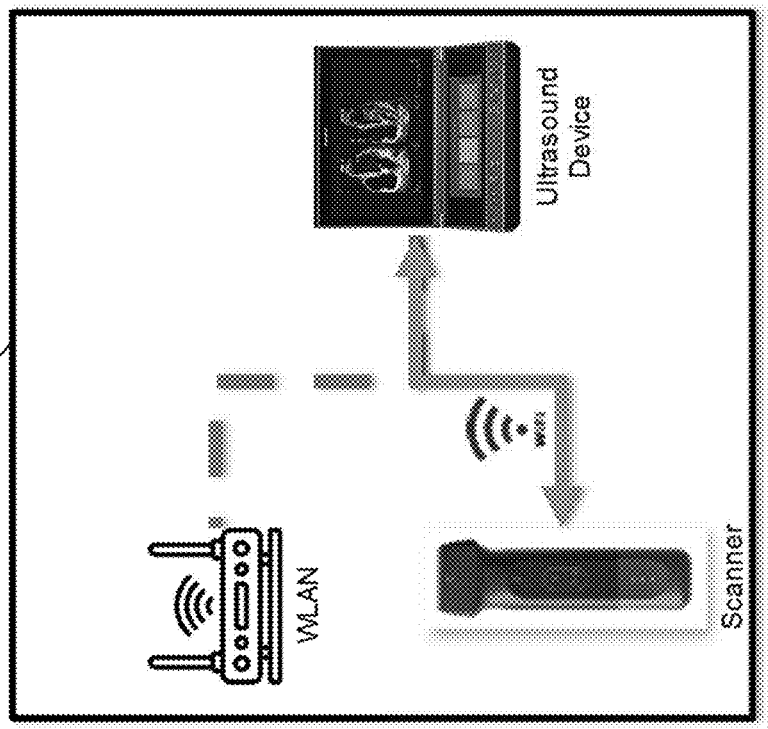

FIG. 2 is a view 200 illustrating connectivity states for another conventional ultrasound system that includes an ultrasound device and a scanner. As shown in FIG. 2, in the connectivity state depicted in insert 201, the ultrasound device is wirelessly connected to the scanner and is disconnected from the WLAN. The wireless connection to the scanner prevents the ultrasound device from connecting to the WLAN and performing all functionality that requires persistent connection to the WLAN, as described above. As shown in FIG. 2, in the connectivity state depicted in insert 202, the ultrasound device is connected to the WLAN and is disconnected from the scanner. The wireless connection to the WLAN prevents the conventional ultrasound device from connecting to the scanner and assessing a patient, as described above. As shown in inserts 201 and 202, the scanner is configured as an end node. In the end node configuration, the scanner, when connected to the display device, can scan a patient, but cannot access a hospital network, while the scanner, when not connected to the display device, cannot scan a patient, but can access a hospital network, as shown in FIGS. 1 and 2.

Currently, without the ability to connect a scanner to a WLAN, direct communication with services used to support the operation of the scanner are blocked. This lack of direct communication means remote updates to the scanner may need to be retained on the handset and uploaded to the scanner when the handset is connected. In some embodiments, the configuration of the scanner as a "hub" with access to the WLAN allows updates and monitoring of the scanner when no handset is present.

Currently, the ability to simultaneously connect a number of scanners to a single handset (or compact ultrasound device) faces a similar challenge of limited Wi-Fi connections. In some embodiments, the configuration that combines scanners into a Wi-Fi mesh, with a single Wi-Fi connection on the handset, provides seamless switching among transducers based on the user's immediate needs.

Figure 3:
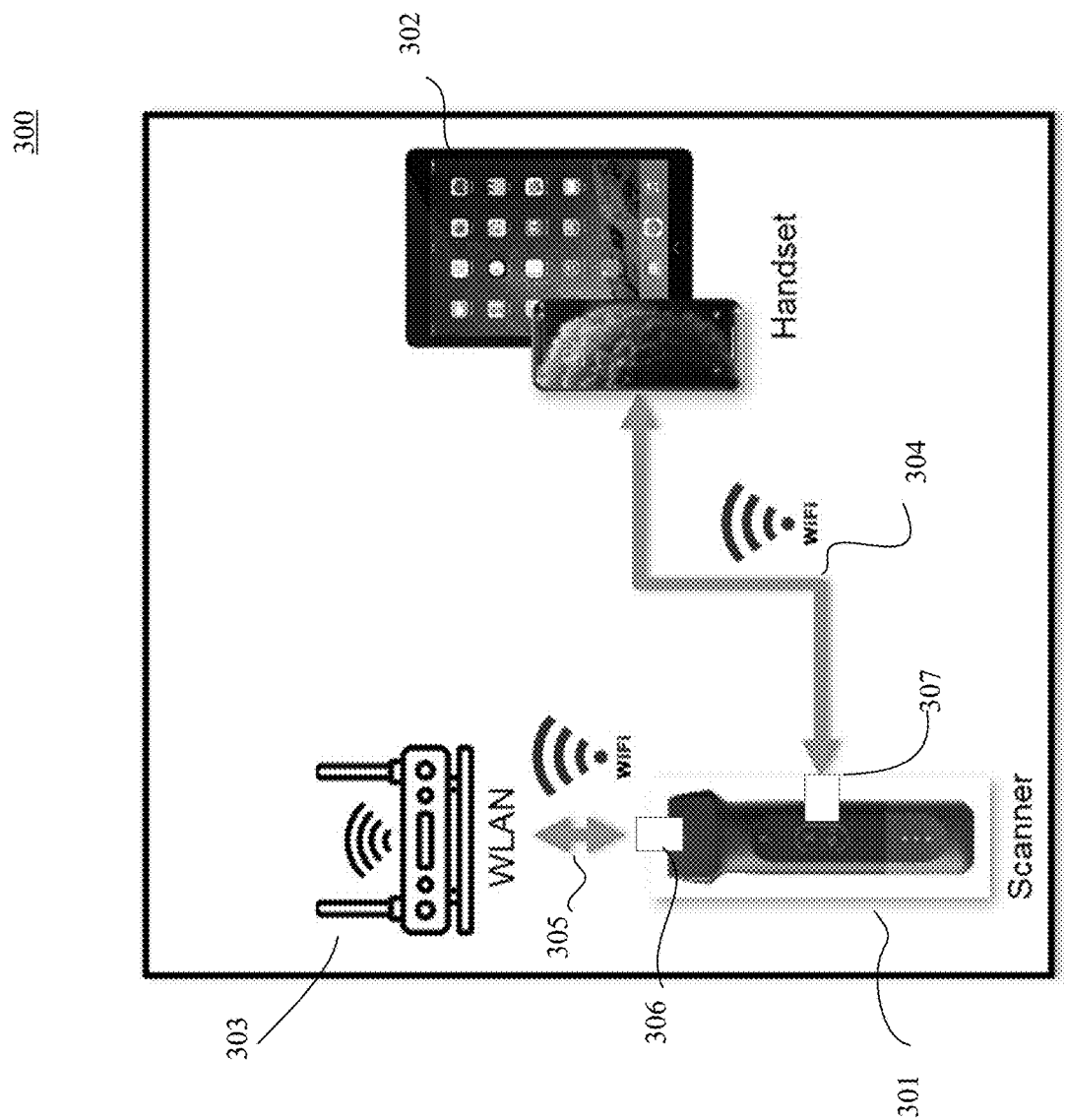
FIG. 3 is a view illustrating an ultrasound system that includes an ultrasound scanner that supports handset wireless connectivity according to some embodiments.

FIG. 3 is a view 300 illustrating an ultrasound system that includes an ultrasound scanner that supports handset wireless connectivity according to some embodiments. In some embodiments, the ultrasound system includes an ultrasound scanner 301 and a compute and visualization system 302, as shown in FIG. 3. In some embodiments, the ultrasound scanner is a wireless scanner. In some embodiments, compute and visualization system 302 is a wireless system. In some embodiments, compute and visualization system 302 is a handset, such as for example, but not limited to, a smartphone, a tablet, and a wireless ultrasound device that includes one or more display devices.

Ultrasound scanner 301 includes a transducer system (not shown) that generates, as part of an ultrasound examination, ultrasound data based on reflections of ultrasound signals transmitted by the transducer system. Ultrasound scanner 301 includes a transceiver 306 and a transceiver 307. In some embodiments, each of transceivers 306 and 307 is implemented at least partially in hardware of ultrasound scanner 301. Transceiver 307 can communicate the ultrasound data over a communication link 304 to a wireless compute and visualization system 302. In some embodiments, wireless compute and visualization system 302 includes one or more display devices that can display an ultrasound image based on the ultrasound data. Transceiver 306 can communicate, over a communication link 305, the ultrasound data through an access point 303 of a wireless network simultaneously with transceiver 307 communicating the ultrasound data via the communication link 304.

As shown in FIG. 3, when connected to a display device of wireless compute and visualization system 302 over communication link 304, scanner 301 in the hub configuration can scan a patient and send the ultrasound data to display on the display device over the communication link 304 and access a hospital network over communication link 305. In some embodiments, scanner 301 in the hub configuration can access a hospital network and scan a patient to send the ultrasound data to display on a display device over communication link 305. For example, the hospital can include a server (not shown in FIG. 3) that is in communication with the access point 303, and the server can be implemented as an ultrasound machine to receive ultrasound data generated by the scanner 301 and, based on the ultrasound data, generate an ultrasound image. The server can then communicate the ultrasound image to any suitable display device that is in communication with the access point 303 (or the hospital network that includes the access point 303), such as a monitor in a patient room. The display device can then display the ultrasound image received from the server via the access point 303 (or a network connected to the access point 303). Hence, the scanner 301 can be in communication via the access point 303 with a centrally-located ultrasound machine in the care facility (e.g., a server) that generates ultrasound images and distributes the ultrasound images via the care facility network to display devices located throughout the care facility.

In some embodiments, one or both of communication links 304 and 305 includes a wireless communication link. Additionally or alternatively, one or both of communication links 304 and 305 can include a wired communication link. In some embodiments, the wireless network that includes access point 303 is a WLAN of a care facility administering the ultrasound examination, or other wireless network. In some embodiments, scanner 301 operates as a client (station) to an access point 303 of the enterprise wireless network and operates as an access point to wireless compute and visualization system 302. In some embodiments, communication link 304 provides ultrasound data to display an ultrasound image on a display of the wireless compute and visualization system 302 and has a priority over the communication link 305. In some embodiments, scanner 301 includes a battery and the priority of communication link 304 and communication link 305 is determined based on the battery level. For example, if the battery level is below a threshold battery level (e.g., less than 15% remaining battery life), the scanner 301 can prioritize the communication link 304 over the communication link 305 so that data from the scanner is communicated more quickly to the handset 302 than to the access point 303. In some embodiments, the communication link 305 provides at least one of a charging parameter, a usage parameter, a configuration parameter, and an update parameter to an ultrasound base station to charge a battery of the ultrasound scanner 301 and has priority over the communication link 304. In some embodiments, the communication link 304 provides at least one of a charging parameter, a usage parameter, a configuration parameter, and an update parameter to an ultrasound base station to charge a battery of the ultrasound scanner 301 and has priority over the communication link 305. In some embodiments, the communication link 304 is more stable and transmits more data per second than the communication link 305. In some embodiments, the communication link 305 is more stable and transmits more data per second than the communication link 304.

In some embodiments, transceiver 306 communicates, over communication link 305, the ultrasound data to an archiver that is coupled to the access point 303 and stores the ultrasound data in a patient record of the ultrasound examination. In some embodiments, transceiver 306 receives, over the communication link 305, one or more configuration update parameters to update a configuration of the ultrasound scanner 301. In some embodiments, transceiver 306 transmits, over the communication link 305, one or more status parameters that indicate a status or usage of the ultrasound scanner 301. In some embodiments, transceiver 306 receives, over the communication link 305, at least one of text, audio, and video, and transceiver 307 transfers, over the communication link 304, the at least one of text, audio, and video to the display device (e.g., handset 302) for user consumption. In some embodiments, transceiver 307 communicates, over another communication link (not shown) and simultaneously with communication over the communication link 304, the ultrasound data to an additional display device (not shown) that displays an additional ultrasound image based on the ultrasound data. In some embodiments, this another communication link is a wireless link; additionally or alternatively, it can include a wired communication link. In some embodiments, the ultrasound examination is implemented as a real-time telemedicine examination and transceiver 306 communicates, over the communication link 305, the ultrasound data to a computing device that is remote from ultrasound scanner 301 and participating in the real-time telemedicine examination. In some embodiments, transceivers 306 and 307 communicate according to the same protocol, and communication links 304 and 305 support communications via the same protocol. For instance, the protocol can include a Wi-Fi protocol.

In some embodiments, ultrasound scanner 301 includes an accelerometer (not shown) that generates inertial movement data of the ultrasound scanner. In some embodiments, at least one of transceivers 306 and 307 initiates communication over communication links 305 and 304, respectively, in response to the inertial movement data representing a gesture. In some embodiments, transceiver 306 turns on communication over communication link 305 in response to the inertial movement data representing a first gesture and turns off communication over communication link 305 in response to the inertial movement data representing a second gesture that is different from the first gesture. In some embodiments, transceiver 307 turns on communication over communication link 304 in response to the inertial movement data representing a first gesture and turns off communication over communication link 304 in response to the inertial movement data representing a second gesture that is different from the first gesture. In some embodiments, ultrasound scanner 301 includes a display that displays a connectivity state of ultrasound scanner 301 with at least one of communication links 304 and 305.

In some embodiments, ultrasound scanner 301 includes a battery (not shown) that is charged by an ultrasound base station that is configured to communicate with the ultrasound scanner 301, over at least one of communication links 304 and 305, one or more of a charging parameter, a usage parameter, a configuration parameter, and an update parameter. In some embodiments, transceiver 306 communicates, over communication link 305 and during the ultrasound examination, the ultrasound data to a server device (not shown) coupled to the access point 303. In some embodiments, the server device includes a neural network that generates an inference based on the ultrasound data. In some embodiments, the inference includes an output of a neural network (e.g., a label, an estimation, a probability, a classification, etc.) In some embodiments, the inference includes an estimation of an imaging part such as a lung, a heart, a liver, or other internal organ. In some embodiments the inference includes an estimation as to whether a detected blood vessel in the ultrasound data is an artery or a vein. In some embodiments, transceiver 306 receives, over communication link 305 and during the ultrasound examination, the inference from the server device. In some embodiments, transceiver 307 communicates, over communication link 304, the inference to the display device of wireless compute and visualization system 302 during the ultrasound examination. Additionally or alternatively, the server can communicate the inference to a display device that is in communication with a hospital network that includes the access point 301. For instance, the server can communicate the inference to a monitor in a patient room, which can display the inference, such as by overlaying the inference on an ultrasound image.

In some embodiments, scanner 301 includes an energy converter (not shown) that transforms movement of the ultrasound scanner into energy and charges a battery of the ultrasound scanner with the energy. In some embodiments, the ultrasound data generated by the scanner includes pre-scan-converted image data and the display device converts the pre-scan-converted image data into scan-converted image data to display the ultrasound data. In some embodiments, a wearable apparatus (not shown), e.g., a holster that can be worn by an operator is used to hold the ultrasound scanner. In some embodiments, at least one display device of the wireless compute and visualization system 302 includes a device having a wearable heads-up display that displays the ultrasound image.

Figure 4:
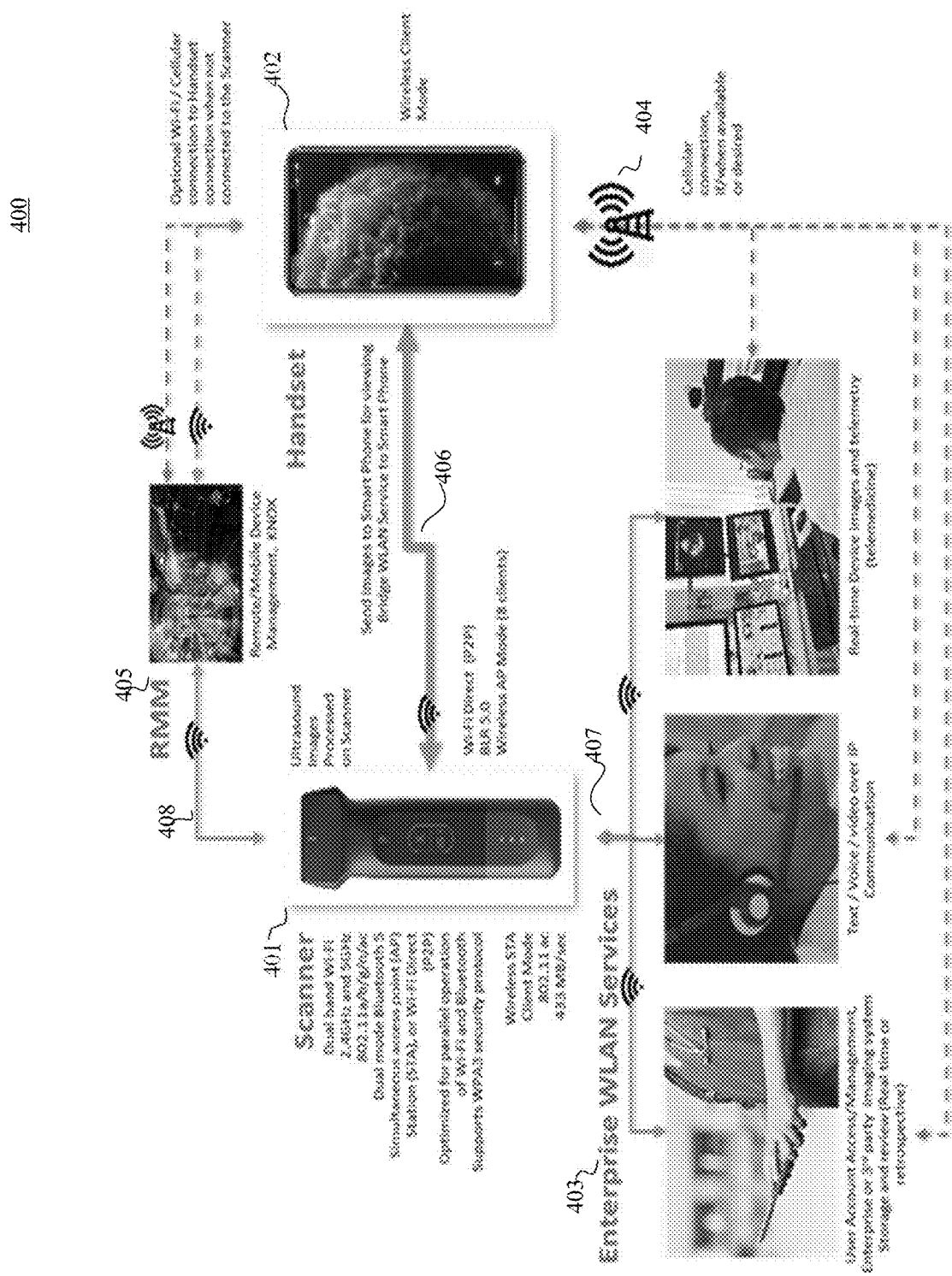
FIG. 4 is a view illustrating an ultrasound system that includes an ultrasound scanner that supports data network communications according to some embodiments.

FIG. 4 is a view illustrating an ultrasound system 400 that includes an ultrasound scanner that supports data network communications according to some embodiments. As shown in FIG. 4, the ultrasound system includes a scanner 401 that operates as a hub that bridges a wireless network 403 via a wireless communication link 407 and a handset 402 via wireless communication link 406. In some embodiments, scanner 401 is scanner 301 of FIG. 3, or another scanner that supports handset wireless network connectivity, as described above. In some embodiments, the scanner is a dual band Wi-Fi scanner that includes transceivers supporting 802.11a/b/g/n/ac wireless networking standard protocols. In some embodiments, the scanner includes one or more transceivers that support 2.4 GHz and 5 GHz bands. In some embodiments, the scanner is a dual mode Bluetooth 5 scanner. In some embodiments, the scanner is a simultaneous access point (AP) a station (STA), or a Wi-Fi Direct (P2P) scanner. In some embodiments, the scanner is configured for parallel operation of Wi-Fi and Bluetooth. In some embodiments, the scanner supports a Wi-Fi Protected Access 3 (WPA3) security protocol. In some embodiments, the scanner operates in a wireless STA client mode according to an 802.11ac wireless networking protocol at 433 MB/sec over communication link 406, communication link 407 or both communication links 406 and 407. In some embodiments, handset 402 represents wireless compute and visualization system 302, or other wireless compute and visualization system, as described above. In some embodiments, scanner 401 includes a first transceiver (not shown) implemented at least partially in hardware of the ultrasound scanner and configured to communicate, over wireless communication link 406, the ultrasound data to a display device of the handset 402 that is configured to display an ultrasound image based on the ultrasound data and a second transceiver (not shown) implemented at least partially in the hardware of the ultrasound scanner and configured to communicate, over wireless communication link 407 and simultaneously with communication over wireless communication link 406, the ultrasound data through an access point of a care facility administering the ultrasound examination that is a part of wireless network 403.

As shown in FIG. 4, scanner 401 is a hub (or bridge) for all data network communication. When connected to a handset 402 via a wireless communication link 406, scanner 401 supports the transfer of scan data/images from the scanner to the handset for viewing, while enabling the data/connections needed to support real-time enterprise WLAN services of the wireless network 403 via a wireless communication link 407 to reach handset 402. Generally, enterprise WLAN Services are services (e.g., VOIP, telemedicine) that are needed while the scanner is connected to the handset.

In some embodiments, wireless communication link 406 is a Wi-Fi Direct (P2P) link, a Bluetooth router (BLR) 5.0 link, a wireless AP mode link, or other wireless communication link. As shown in FIG. 4, wireless network 403 includes the real time Enterprise WLAN services, for example, a user account access/management, Enterprise or third-party imaging system storage and review (real time or retrospective), text, voice, video over IP (VOIP) communication, real-time device images and telemetry (telemedicine), and other real time services. In some embodiments, wireless network 403 includes an access point of a care facility administering the ultrasound examination (not shown), such as access point 303 of FIG. 3. The scanner can be contacted directly via a wireless communication link 408 by a remote monitoring and management (RMM) system 405 to support software and status updates. In some embodiments, RMA/1 system 405 is a part of the wireless network 403, and the scanner can be contacted via wireless communication link 407 by RMM system 405 with software and status updates. In some embodiments, RMA/1 system 405 includes, but is not limited to, delivery and installation of remote updates, device location monitoring, scanner access control (if lost or stolen). In some embodiments, RMM system 405 can provide manufacturer specific services used to assess and maintain the proper operation and physical condition of the scanner. In some embodiments, the RMA/1 includes a remote/mobile device management system, e.g., a KNOX manage, or other remote/mobile device management system. As shown in FIG. 4, handset 402 becomes a client on the network created by the scanner 401. The handset 402 can connect to WLAN when not connected to the scanner. In some embodiments, a cellular data connection is supported, while in other embodiments, such a connection is not included.

Figure 5:
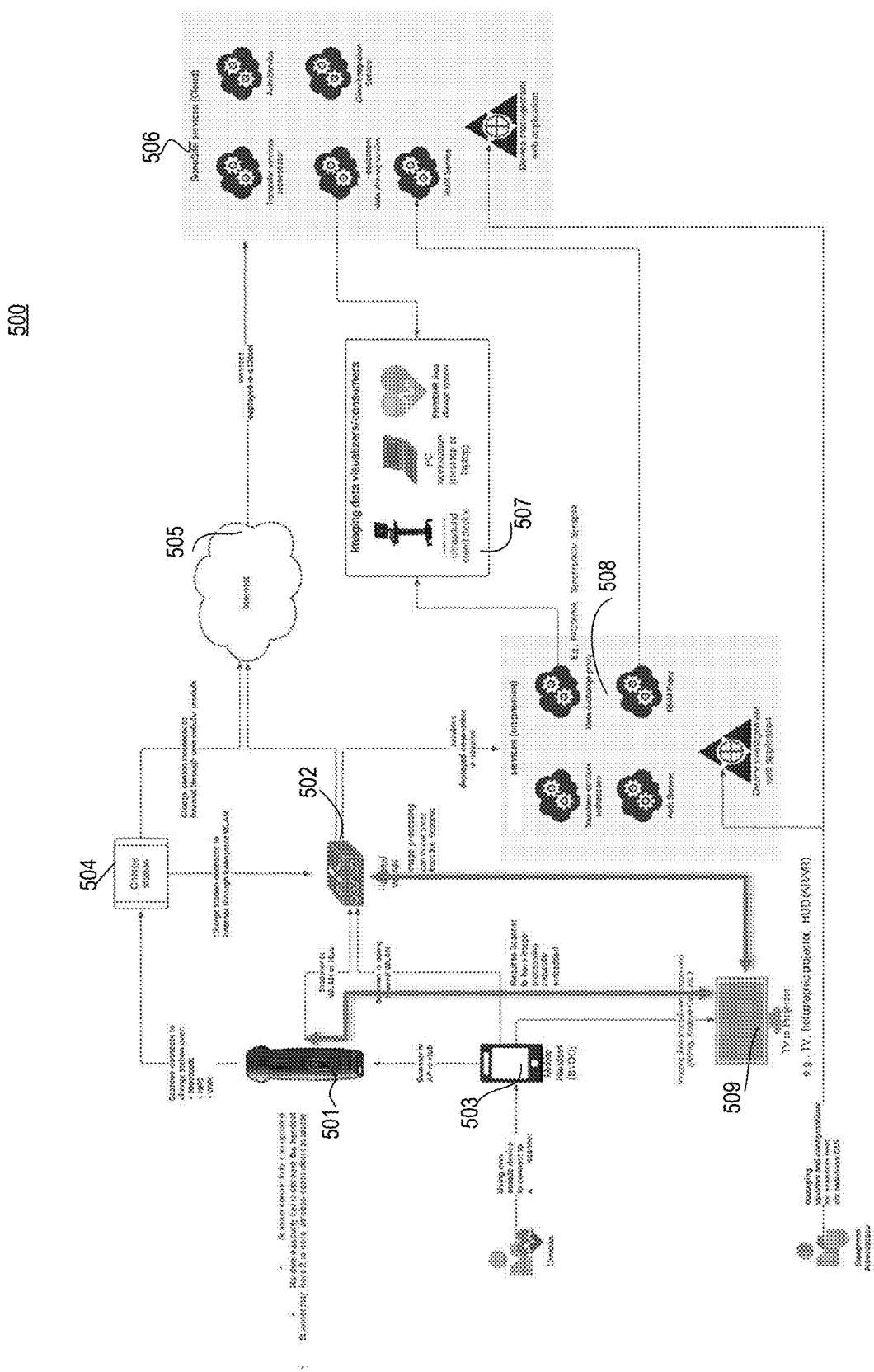
FIG. 5 is a view illustrating an ultrasound system that includes an ultrasound scanner that supports data network communications according to some embodiments.

FIG. 5 is a view illustrating an ultrasound system 500 that includes an ultrasound scanner 501 that supports data network communications according to some embodiments. Scanner 501 has two or more wireless connections available, such as scanners as described above. As shown in FIG. 5, the ultrasound system 500 includes an ultrasound scanner 501 that is connected to an enterprise WLAN 502, a mobile handset 503 and a base station 504. In some embodiments, scanner 501 represents one of the scanners that supports handset wireless network connectivity, as described above. In some embodiments, mobile handset 503 represents one of the wireless compute and visualization systems described herein. In some embodiments, the scanner operates as a hub or a part of WLAN to connect to WLAN 502. In some embodiments, scanner 501 uses the WLAN that is shared with handset 503. In some embodiments, scanner 501 operates as an AP or a hub to connect to the mobile handset 503. In some embodiments, enterprise WLAN 502 is a hospital WLAN or other enterprise WLAN.

In some embodiments, base station 504 charges a battery of the ultrasound scanner 501 and communicates with ultrasound scanner 501 over a communication link. In some embodiments, this communication link is a Bluetooth link, a Wi-Fi link, a near field communication (NFC) link, or other wireless communication link. In some embodiments, base station 504 connects to Internet 505 through enterprise WLAN 502. In some embodiments, base station 504 connects to Internet 505 through its own enterprise cellular module. A clinician can use their own mobile handset to connect to the scanner. The imaging data from handset 503 can be shared over a screen cast (e.g., AirPlay, Android Cast, etc.) on a display device 509. In some embodiments, display device 509 is a television (TV), a holographic projector, or other display device. In some embodiments, an image processing capability is embedded into the scanner and the scanner sends ultrasound images to display on display device 509. In some embodiments, image processing is performed away from scanner 501 and images are sent from enterprise WLAN 502 for displaying on display device 509. In some embodiments, display device 509 displays an ultrasound image based on ultrasound data received from the scanner. In some embodiments, the ultrasound data from the scanner 501 includes pre-scan-converted image data and the display device 509 converts the pre-scan-converted image data into scan-converted image data to display the ultrasound data.

As shown in FIG. 5, enterprise WLAN 502 is connected to on-premises enterprise services 508 that include a translator services orchestrator, a data exchange proxy (e.g., picture archiving and communication system (PACs), Vendor Neutral Archive (VNA), Synchronicity, Synapse), an authentication service, RMM proxy and device management web application. In some embodiments, the scanner connectivity state is updated. As shown in FIG. 5, managing updates and configurations for a fleet of scanners are sent by an equipment administrator via a web-based graphical user interface (GUI) to the device management application of the on-premise enterprise services 508. In some embodiments, an enterprise network security/authentication key is stored in handset 503 and transferred to the scanner 501 via handset-scanner link. In some embodiments, an enterprise network security/authentication key is stored in the scanner 501.

As shown in FIG. 5, the data exchange proxy of the on-premise enterprise services 508 is connected to imaging data visualizers/consumer systems 507. In some embodiments, imaging data visualizers/consumer systems 507 include one or more of an ultrasound stand device, a personal computer (PC) workstation (e.g., desktop or laptop), an electronic health records (EHR) and an electronic medical records (EMR) data storage system. As shown in FIG. 5, imaging data visualizers/consumer systems 507 are connected to both on-premise services 508 and cloud services 506 to access and visualize ultrasound data. Imaging data visualizers/consumer systems 507 and a display of mobile handset 503 provide viewing on multiple displays an ultrasound image generated using a single scanner.

As shown in FIG. 5, each of enterprise WLAN 502 and base station 504 is connected via Internet 505 to services on a cloud 506. In some embodiments, the cloud includes a translator services orchestrator, an authentication service, an equipment data sharing service, a clinic integration service, an RMM service and a device management web application. As shown in FIG. 5, the RMM service of the cloud 506 is connected to RMM proxy of the services deployed on-premise services 508 (e.g., in the hospital). As shown in FIG. 5, managing updates and configurations for scanners fleet are sent by an equipment administrator via a web-based graphical user interface (GUI) to the device management web application on cloud 506.

Figure 6:
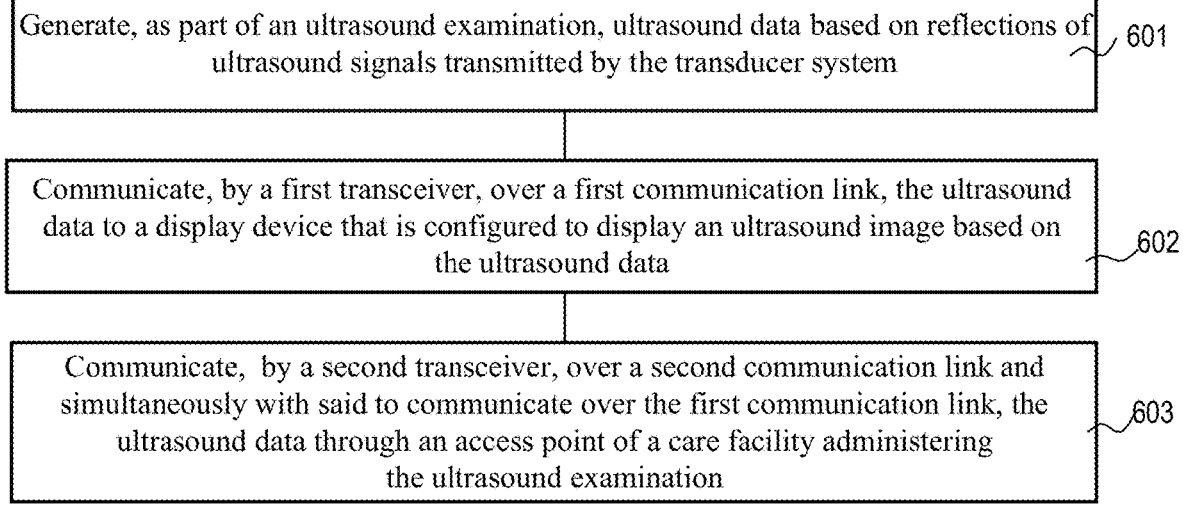
FIG. 6 is a data flow diagram of a process implemented by an ultrasound scanner to perform an ultrasound examination according to some embodiments.

FIG. 6 is a data flow diagram of a process 600 implemented by an ultrasound scanner to perform an ultrasound examination according to some embodiments. The process is performed by processing logic that may comprise hardware (circuitry, dedicated logic, etc.), software (such as is run on a general-purpose computer system or a dedicated machine), firmware, or combinations thereof. In some embodiments, the ultrasound scanner includes a transducer system that generates, as part of an ultrasound examination, ultrasound data based on reflections of ultrasound signals transmitted by the transducer system, a first transceiver implemented at least partially in hardware of the ultrasound scanner that communicates, over a first communication link, the ultrasound data to a display device that displays an ultrasound image based on the ultrasound data, and a second transceiver implemented at least partially in the hardware of the ultrasound scanner that communicates, over a second communication link and simultaneously with the first transceiver communicating over the first communication link, the ultrasound data through an access point of a care facility administering the ultrasound examination, as described above. In some embodiments, the ultrasound scanner includes one or more processors and a memory coupled to the processor(s) to perform the process 600.

Referring to FIG. 6, process 600 includes processing logic generating, as part of an ultrasound examination, ultrasound data based on reflections of ultrasound signals transmitted by the transducer system at block 601. Process 600 continues at block 602 where processing logic communicates, using a first transceiver, over a first communication link, the ultrasound data to a display device that is configured to display an ultrasound image based on the ultrasound data. At block 603, processing logic communicates, using a second transceiver, over a second communication link and simultaneously with the first transceiver communicating over the first communication link, the ultrasound data through an access point of a care facility administering the ultrasound examination. In some embodiments, processing logic communicates, using the second transceiver, over the second communication link, the ultrasound data to an archiver that is coupled to the access point and stores the ultrasound data in a patient record of the ultrasound examination. In some embodiments, processing logic receives, using the second transceiver, over the second communication link, one or more configuration update parameters to update a configuration of the ultrasound scanner, as described above. In some embodiments, processing logic transmits, using the second transceiver over the second communication link, one or more status parameters that indicate a status or usage of the ultrasound scanner. In some embodiments, processing logic receives, using the second transceiver over the second communication link, at least one of text, audio, and video, and the first transceiver is implemented to transfer, over the first communication link, the at least one of text, audio, and video to the display device for user consumption. In some embodiments, processing logic communicates, using the first transceiver over a third communication link and simultaneously with communicating over the first communication link, the ultrasound data to an additional display device that displays an additional ultrasound image based on the ultrasound data.

In some embodiments, the ultrasound examination is a real-time telemedicine examination and processing logic communicates, via the second transceiver over the second communication link, the ultrasound data to a computing device that is remote from the ultrasound scanner and participating in the real-time telemedicine examination. In some embodiments, the first transceiver and the second transceiver communicate according to the same protocol, and the first communication link and the second communication link support communications via the same protocol. In some embodiments, processing logic generates, using an accelerometer, inertial movement data of the ultrasound scanner, and initiates, using at least one of the first transceiver and the second transceiver, communication over the first communication link and the second communication link, respectively, responsive to the inertial movement data representing a gesture. In some embodiments, processing logic displays a connectivity state of the ultrasound scanner with at least one of the first communication link and the second communication link on a display device. In some embodiments, processing logic communicates at least one of a charging parameter, a usage parameter, a configuration parameter, and an update parameter with an ultrasound base station over at least one of the first communication link and the second communication link to charge a battery of the ultrasound scanner. In some embodiments, processing logic communicates, using the second transceiver over the second communication link and during the ultrasound examination, the ultrasound data to a server device coupled to the access point and that implements a neural network to generate an inference based on the ultrasound data; and processing logic receives, over the second communication link and during the ultrasound examination, the inference from the server device. In some embodiments, processing logic communicates, using the first transceiver, over the first communication link, the inference to the display device during the ultrasound examination, as described above.

Embodiments described herein support the simultaneous acquisition and transfer of data in real time, while maintaining the communication connection to the hospital network, allow the use of handsets that support only a single Wi-Fi connection to the hospital network, without requiring costly and rare handsets having multi-point Wi-Fi connectivity, or some other third-party Wi-Fi bridging solution. Embodiments described herein make the user experience of operating a wireless scanner consistent with that of operating a conventional ultrasound system having a wired probe, improve user experience, and provide superior patient care compared to ultrasound systems having conventional wireless scanners.

The ability to connect a scanner to a handset while maintaining a WLAN connection that supports the user's workflow offer significant advantages over conventional scanners for the consistency the user experience when using an ultraportable-class ultrasound device for different mobile operating systems (e.g., iOS, Android).

It is apparent from this description that embodiments described herein may be embodied, at least in part, in software. That is, the techniques and methods may be carried out in a data processing system or set of data processing systems in response to one or more processors executing a sequence of instructions stored in a storage medium, such as a non-transitory machine-readable storage media, such as volatile DRAM or nonvolatile flash memory. In various embodiments, hardwired circuitry may be used in combination with software instructions to implement the embodiments described herein. Thus, the techniques and methods are not limited to any specific combination of hardware circuitry and software, or to any particular source for the instructions executed by the one or more data processing systems.

In the foregoing specification, specific exemplary embodiments have been described. It will be evident that various modifications may be made to those embodiments without departing from the broader spirit and scope set forth in the following claims. The specification and drawings are, accordingly, to be regarded in an illustrative sense rather than a restrictive sense.

What is claimed is:

1. An ultrasound scanner comprising:
a transducer system configured to generate, as part of an ultrasound examination, ultrasound data based on reflections of ultrasound signals transmitted by the transducer system;
a first transceiver implemented at least partially in hardware of the ultrasound scanner and configured to communicate, over a first communication link, the ultrasound data to a display device that is external to the ultrasound scanner and configured to display an ultrasound image based on the ultrasound data; and
one or more additional transceivers implemented at least partially in the hardware of the ultrasound scanner and coupled to the first transceiver and configured to communicate, over one or more additional communication links the ultrasound data through a network access point of a wireless local area network (WLAN) simultaneously with said first transceiver communicating the ultrasound data over the first communication link, wherein the ultrasound scanner is an ultrasound probe that operates as a hub that bridges the WLAN via the one or more additional communication links to the display device via the first communication link.

2. The ultrasound scanner as described in claim 1, wherein the one or more additional transceivers is implemented to communicate, over the one or more additional communication links, the ultrasound data to an archiver that is coupled to the access point and configured to store the ultrasound data in a patient record of the ultrasound examination.

3. The ultrasound scanner as described in claim 1, wherein the one or more additional transceivers is implemented to receive, over the one or more additional communication links, one or more configuration update parameters to update a configuration of the ultrasound scanner.

4. The ultrasound scanner as described in claim 1, wherein the one or more additional transceivers is implemented to transmit, over the one or more additional communication links, one or more status parameters that indicate a status or usage of the ultrasound scanner.

5. The ultrasound scanner as described in claim 1, wherein the one or more additional transceivers is implemented to receive, over the one or more additional communication links, at least one of text, audio, and video, and the first transceiver is implemented to transfer, over the first communication link, the at least one of text, audio, and video to the display device for user consumption.

6. The ultrasound scanner as described in claim 1, wherein the first transceiver is implemented to communicate, over a third communication link and simultaneously with said to communicate over the first communication link, the ultrasound data to an additional display device that is configured to display an additional ultrasound image based on the ultrasound data.

7. The ultrasound scanner as described in claim 1, wherein the ultrasound examination is implemented as a real-time telemedicine examination and the one or more additional transceivers is implemented to communicate, over the one or more additional communication links, the ultrasound data to a computing device that is remote from the ultrasound scanner and participating in the real-time telemedicine examination.

8. The ultrasound scanner as described in claim 1, wherein the first transceiver and the one or more additional transceivers are implemented to communicate according to a same protocol, and the first communication link and the one or more additional communication links are implemented to support communications via the same protocol.

9. The ultrasound scanner as described in claim 1, further comprising an accelerometer configured to generate inertial movement data of the ultrasound scanner, wherein at least one of the first transceiver and the one or more additional transceivers is configured to initiate communication over the first communication link and the one or more additional communication links, respectively, responsive to the inertial movement data representing a gesture.

10. The ultrasound scanner as described in claim 1, further comprising a display configured to display a connectivity state of the ultrasound scanner with at least one of the first communication link and the one or more additional communication links.

11. The ultrasound scanner as described in claim 1, further comprising a battery configured to be charged by an ultrasound base station that is configured to communicate with the ultrasound scanner over at least one of the first communication link and the one or more additional communication links, including to communicate at least one of a charging parameter, a usage parameter, a configuration parameter, and an update parameter.

12. The ultrasound scanner as described in claim 1, wherein the one or more additional transceivers is implemented to:
communicate, over the one or more additional communication links and during the ultrasound examination, the ultrasound data to a server device coupled to the access point, wherein the server device implements a neural network configured to generate an inference based on the ultrasound data; and
receive, over the one or more additional communication links and during the ultrasound examination, the inference from the server device.

13. The ultrasound scanner as described in claim 12, wherein the first transceiver is implemented to communicate, over the first communication link, the inference to the display device during the ultrasound examination.

14. The ultrasound scanner as described in claim 1, further comprising an energy converter configured to transform movement of the ultrasound scanner into energy and charge a battery of the ultrasound scanner with the energy.

15. An ultrasound system comprising:
at least one display device that is configured to display an ultrasound image based on ultrasound data; and
an ultrasound scanner configured to, as part of an ultrasound examination:
generate the ultrasound data based on reflections of ultrasound signals transmitted by the ultrasound scanner, wherein ultrasound scanner includes a first transceiver and one or more additional transceivers coupled to the first transceiver, wherein the ultrasound scanner is configured to:
communicate, over a first communication link, the ultrasound data to the at least one display device external to the ultrasound scanner using the first transceiver; and
communicate, over one or more additional communication links the ultrasound data through an access point of a wireless local area network (WLAN) of a care facility administering the ultrasound examination using the one or more additional transceivers simultaneously with said first transceiver communicating the ultrasound data over the first communication link, wherein the ultrasound scanner is an ultrasound probe that operates as a hub that bridges the WLAN via the one or more additional communication links to the at least one display device via the first communication link.

16. The ultrasound system as described in claim 15, further comprising a base station configured to charge a battery of the ultrasound scanner and communicate with the ultrasound scanner over at least one of the first communication link and the one or more additional communication links.

17. The ultrasound system as described in claim 15, wherein the ultrasound data includes pre-scan-converted image data and the at least one display device is implemented to convert the pre-scan-converted image data into scan-converted image data to display the ultrasound data.

18. The ultrasound system as described in claim 15, further comprising a wearable apparatus configured to hold the ultrasound scanner.

19. The ultrasound system as described in claim 15, wherein the at least one display device includes a device having a wearable heads-up display configured to display the ultrasound image.

20. A method implemented by an ultrasound scanner including a first transceiver and one or more additional transceivers coupled to the first transceiver to perform an ultrasound examination, the method comprising:
generating ultrasound data based on reflections of ultrasound signals transmitted by the ultrasound scanner;
communicating, over a first communication link, the ultrasound data to at least one display device external to the ultrasound scanner and configured to display an ultrasound image based on the ultrasound data using the first transceiver; and communicating, over one or more additional communication links the ultrasound data through a network access point of a wireless local area network (WLAN) of a care facility administering the ultrasound examination using the one or more additional transceivers simultaneously with said first transceiver communicating the ultrasound data over the first communication link, wherein the ultrasound scanner is an ultrasound probe that operates as a hub that bridges the WLAN via the one or more additional communication links to the at least one display device via the first communication link.

* * * * *